United States Patent
Wang

(10) Patent No.: US 9,183,628 B2
(45) Date of Patent: Nov. 10, 2015

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Caihua Wang, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 14/309,482

(22) Filed: Jun. 19, 2014

(65) Prior Publication Data

US 2014/0301623 A1 Oct. 9, 2014

Related U.S. Application Data

(63) Continuation of application No. PCT/JP2012/008000, filed on Dec. 14, 2012.

(30) Foreign Application Priority Data

Dec. 20, 2011 (JP) ................................. 2011-278239
Nov. 6, 2012 (JP) ................................. 2012-244542

(51) Int. Cl.
*G06T 7/00* (2006.01)
*A61B 5/055* (2006.01)
(Continued)

(52) U.S. Cl.
CPC ............. *G06T 7/0012* (2013.01); *A61B 5/0042* (2013.01); *A61B 5/055* (2013.01); *A61B 6/5235* (2013.01); *G06T 3/0093* (2013.01);
(Continued)

(58) Field of Classification Search
None
See application file for complete search history.

(56) References Cited

U.S. PATENT DOCUMENTS 5,633,951 A * 5/1997 Moshfeghi ................... 382/154
2006/0029291 A1 2/2006 Sun et al.
(Continued)

FOREIGN PATENT DOCUMENTS

JP H 06-337922 A 12/1994
JP 2007-159933 A 6/2007
(Continued)

OTHER PUBLICATIONS

Wang et al. "Elastic & Efficient Three-Dimensional Registration for Abdominal Images." Sixth International Conference on Intelligent Systems Design and Applications, Oct. 16, 2006, pp. 502-507.*
(Continued)

*Primary Examiner* — Jon Chang
(74) *Attorney, Agent, or Firm* — McGinn IP Law Group, PLLC

(57) ABSTRACT

A first image and a second image are obtained; the amount of deformation of the first image is estimated by evaluating the degree of similarity between a deformed first image and the second image, using an evaluation function that evaluates the correlation between the distribution of corresponding pixel values within the two images; and an image, which is the first image deformed based on the estimated amount of deformation, is generated. The evaluation function evaluates the degree of similarity between the deformed first image and the second image, based on degrees of similarities of divided images that represent degrees of similarities among the distributions of pixel values of each pair of divided first images and divided second images, which respectively are images that the deformed first image is divided into and images that the second image is divided into, according to predetermined dividing conditions.

9 Claims, 6 Drawing Sheets

(51) Int. Cl.
    *A61B 5/00* (2006.01)
    *G06T 3/00* (2006.01)
    *A61B 6/00* (2006.01)

(52) U.S. Cl.
    CPC ............... *G06T 7/003* (2013.01); *A61B 6/501* (2013.01); *A61B 2576/00* (2013.01); *A61B 2576/026* (2013.01); *G06T 2207/10081* (2013.01); *G06T 2207/20021* (2013.01); *G06T 2207/30016* (2013.01)

(56) References Cited

U.S. PATENT DOCUMENTS

2008/0298657 A1* 12/2008 Shiraishi et al. .............. 382/130
2008/0312527 A1   12/2008 Masumoto et al.

FOREIGN PATENT DOCUMENTS

JP   2008-289799 A   12/2008
JP   2011-024763 A   2/2011

OTHER PUBLICATIONS

Li et al. "Non-rigid Image Registration based on Overlapped Block Check and Free-Form Deformation." 3rd International Congress on Image and Signal Processing, Oct. 16, 2010, pp. 2810-2814.*
Krücker et al. "Rapid Elastic Image Registration for 3-D Ultrasound." IEEE Transactions on Medical Imaging, vol. 21, No. 11, Nov. 2002, pp. 1384-1394.*
Ahmad et al. "Deformable Rigid Body Hausdorff Registration for Multi-modal Medical Images." IEEE Region 10 Conference, Jan. 23, 2009, pp. 1-6.*
Japanese Office Action dated Mar. 24, 2015 with a partial English translation thereof.
International Search Report (ISR) (PCT Form PCT/ISA/210), in PCT/JP2012/008000, dated Apr. 2, 2013.
D. Mattes et al., "Nonrigid multhnodality image registration", Proceedings of the SPIE, vol. 4322, pp. 1609-1620, 2001.
C. Lin et al., "PCA Based Regional Mutual Information for Robust Medical Image Registration", IEICE Technical Report, vol. 109, No. 65, pp. 23-28, 2009.

* cited by examiner

FIG.4A
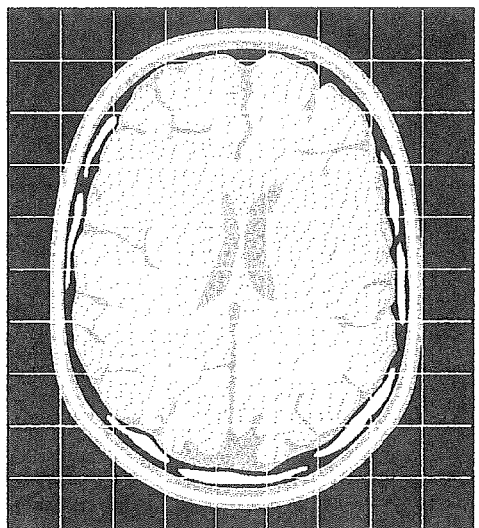
V1
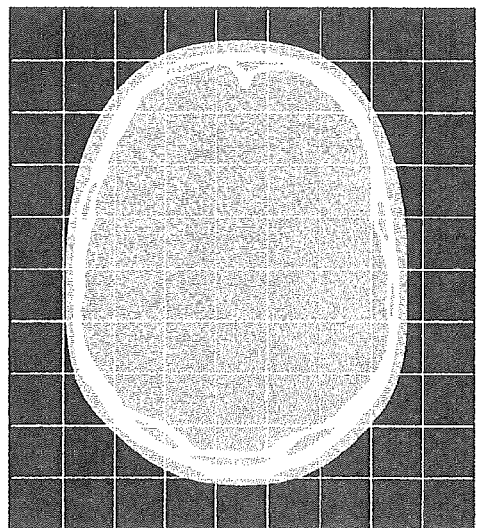
V2
FIG.4B
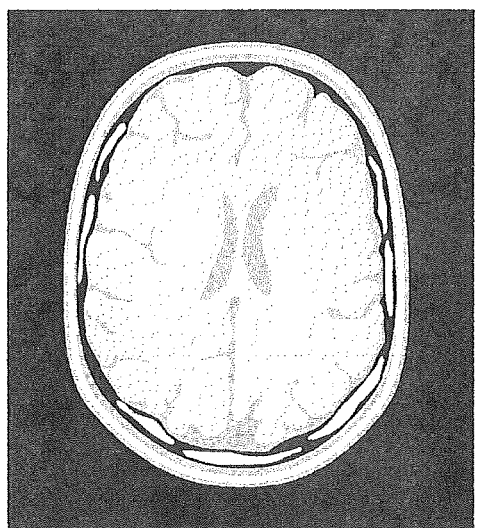
V1A
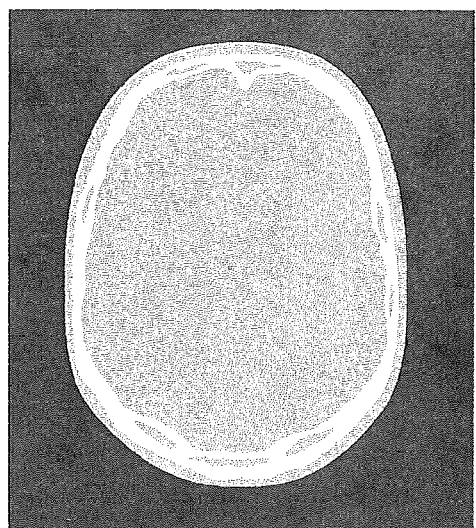
V2

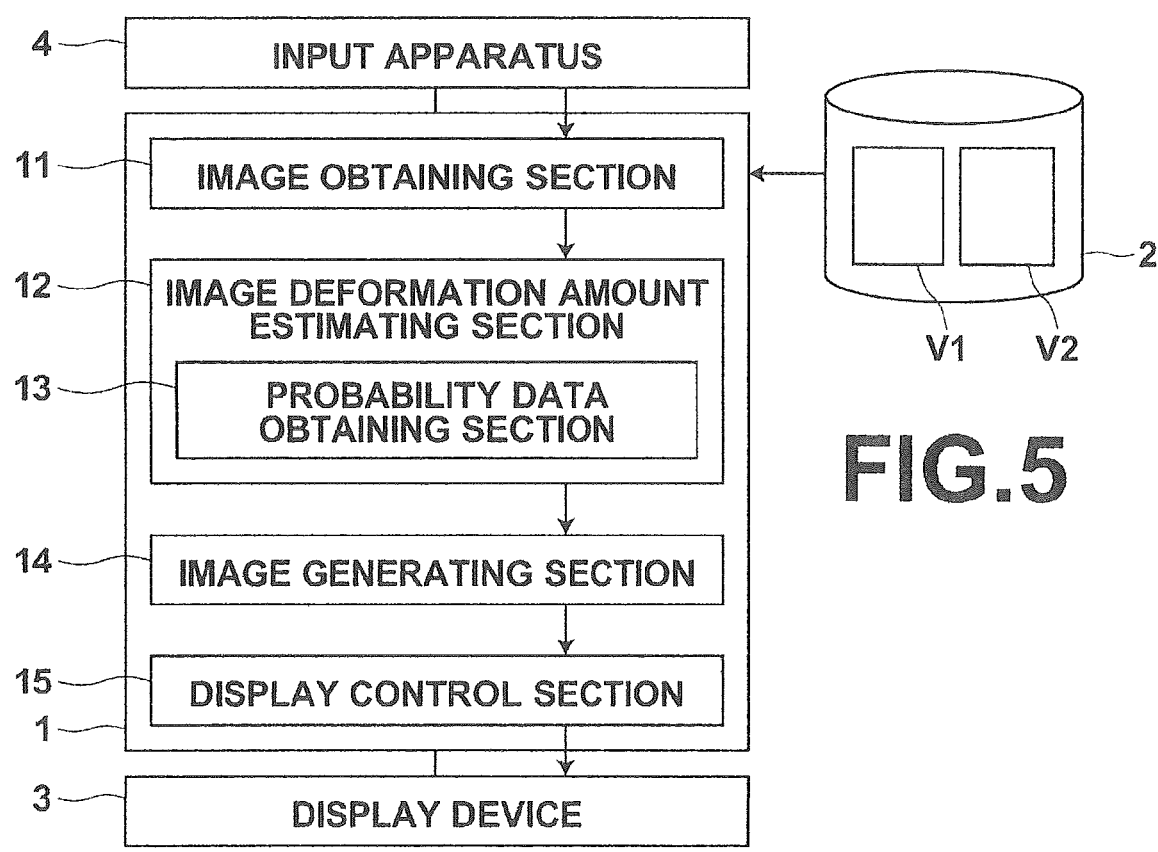

IMAGE PROCESSING APPARATUS, IMAGE PROCESSING METHOD, AND IMAGE PROCESSING PROGRAM

CROSS REFERENCE TO RELATED APPLICATIONS

This application is a Continuation of PCT International Application No. PCT/JP2012/008000 filed on Dec. 14, 2012, which claims priority under 35 USC 5119(a) to Japanese Patent Application No. 2011-278239 filed on Dec. 20, 2011 and Japanese Patent Application No. 2012-244542 filed on Nov. 6, 2012. Each of the above applications is hereby expressly incorporated by reference, in its entirety, into the present application.

TECHNICAL FIELD

The present invention is related to an image processing apparatus, an image processing method, and an image processing program that generate an image, which is one of two images obtained by imaging a single subject, of which the image space has been deformed, such that the spatial positions of subjects within the two images match.

BACKGROUND ART

The non rigid registration technique, in which a converting function that causes spatial positions of subjects within two three dimensional images that are obtained by imaging a single subject using the same or different imaging apparatuses (modalities) at different timings to match is estimated, and the two types of images are registered by deforming one of the images using the estimated converting function, is being focused on in the field of image diagnosis. The non rigid registration technique sets control points that section image spaces at predetermined intervals. The positions of the control points are displaced, and an amount of image deformation at which the value of an evaluation function that evaluates the degree of similarity among pixel values of a deformed first image and a second image becomes maximal is determined. The converting function is estimated based on the amount of image deformation using the control points in such a state.

The invention disclosed in D. Mattes et al., "Nonrigid Multimodality Image Registration", Proceedings of the SPIE, Vol. 4322, pp 0.1609-1620, 2001 applies the non rigid registration process to images of the same subject obtained by a PET (Positron Emission Tomography) apparatus and a CT (Computed Tomography) apparatus. The invention disclosed in D. Mattes et al., employs mutual information as a measure of the degrees of similarity among pixel values within the two types of images.

DISCLOSURE OF THE INVENTION

However, in the method disclosed in D. Mattes et al., the degree of similarity between two images is judged based only on the correlative properties between the distributions of pixel values within the two images. Therefore, spatial characteristics of the images cannot be judged, and there are cases in which the judgment of similarity is erroneous.

For example, the method disclosed in D. Mattes et al., will judge that two images, in which a plurality of subjects belonging to the same range of pixel values are imaged, are similar in the case that the total number of pixels belonging to the same range of pixel values are the same within the two images, even if the numbers or the spatial positions of the plurality of subjects are different. Specifically, the pixel values of pixels that represent a pancreas and a liver within a first image obtained by imaging the thoracic region of a patient belong to the same predetermined range of pixel values. If there is a single pattern having pixel values within the predetermined range of pixel values within a second image of the thoracic region of the same patient, there is a possibility that the method disclosed in D. Mattes, et al. will judge that the two images are similar, in the case that the volume of the pattern is equal to the sum of the volumes of the liver and the pancreas within the first image.

The present invention has been developed in view of the aforementioned problem. It is an object of the present invention to provide an image processing apparatus, an image processing method, and an image processing program that accurately evaluate degrees of similarity between images that include a plurality of subjects belonging to the same range of pixel values, by reflecting spatial features of the subjects in the evaluation of the degrees of similarity, and which are capable of generating an image, which is one of the images deformed such that the subjects match more precisely.

An image processing apparatus that achieves the above objective comprises:

an image obtaining section that obtains a first image and a second image which are obtained by imaging the same subject at different timings;

an image deformation amount estimating section that estimates an amount of deformation of the first image by deforming the first image and evaluating the degree of similarity between the deformed first image and the second image using an evaluation function that evaluates the correlative properties between the distribution of pixel values within the deformed first image and the distribution of pixel values within the second image corresponding thereto; and an image generating section that generates an image, which is the first image deformed based on the estimated amount of deformation;

the evaluation function evaluating the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images.

An image processing method of the present invention is an image processing method to be executed by the above image processing apparatus, and comprises:

obtaining a first image and a second image which are obtained by imaging the same subject at different timings;

estimating an amount of deformation of the first image by deforming the first image and evaluating the degree of similarity between the deformed first image and the second image using an evaluation function that evaluates the correlative properties between the distribution of pixel values within the deformed first image and the distribution of pixel values within the second image corresponding thereto; and generating an image, which is the first image deformed based on the estimated amount of deformation;

the evaluation function evaluating the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images.

An image processing program of the present invention causes a computer to function as:

an image obtaining section that obtains a first image and a second image which are obtained by imaging the same subject at different timings;

an image deformation amount estimating section that estimates an amount of deformation of the first image by deforming the first image and evaluating the degree of similarity between the deformed first image and the second image using an evaluation function that evaluates the correlative properties between the distribution of pixel values within the deformed first image and the distribution of pixel values within the second image corresponding thereto; and an image generating section that generates an image, which is the first image deformed based on the estimated amount of deformation;

the evaluation function evaluating the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images.

In the image processing apparatus, the image processing method, and the image processing program of the present invention, the first image and the second image may be those obtained by imaging with the same modality or those obtained by imaging with different modalities, as long as they are obtained by imaging the same subject. In addition, examples of modalities that may be applied as a first and a second modality include: PET, CT, MRI, SPECT, and ultrasound images.

In the image processing apparatus of the present invention, the evaluation function may be any function as long it evaluates the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images. For example, the evaluation function may be defined such that evaluation values become greater as the two images are more similar. Alternatively, the evaluation function may be defined such that evaluation values become smaller as the two images are more similar.

In the image processing apparatus of the present invention, it is preferable for the evaluation function to represent an amount of mutual information, in which the pixel values of the deformed first image and the pixel values of the second image are discrete random variables.

The dividing conditions may be any conditions as long as they are capable of dividing the deformed first image and the second image based on predetermined rules.

As an example, it is preferable for the dividing conditions to be those that divide the deformed first image into a plurality of divided first images based on a predetermined first spatial parameter, and divide the second image into a plurality of divided second images that correspond to the divided first images based on a second spatial parameter corresponding to the first spatial parameter, in the image processing apparatus of the present invention.

In the image processing apparatus of the present invention, the first spatial parameter may represent the distance from a predetermined shape within the first image, and the second spatial parameter may represent the distance from a shape within the second image corresponding to the predetermined shape.

In this case, it is preferable for the predetermined shape to be a point, and for the dividing conditions to be those that divide the first image for each range of the first spatial parameter according to the first spatial parameter, and divide the second image for each range of the second spatial parameter, which corresponds to the range of the first spatial parameter.

Alternatively, in the image processing apparatus of the present invention, it is preferable for the first spatial parameter to represent an angle with respect to a predetermined shape within the first image, and for the second spatial parameter to represent an angle with respect to a shape within the second image corresponding to the predetermined shape.

In this case, it is preferable for the predetermined shape to be a predetermined axis within the first image, for the first spatial parameter to represent an angle from the predetermined axis within the first image, and for the second spatial parameter to represent an angle from an axis within the second image corresponding to the predetermined axis.

The predetermined axis may be set as desired by a user. Examples of the predetermined axis include an xy plane and the x, y, and z axes in an xyz coordinate system.

Note that here, the shape refers to a shape which is determined according to a predetermined rule. Examples of the shape include: a point, a line, a curve, a three dimensional shape such as a sphere, and a portion of a three dimensional shape. The shapes that correspond to each other within the first image and the second image may be arbitrarily defined as a curve, a three dimensional shape such as a sphere, or a portion of a three dimensional shape. However, it is necessary for the corresponding shapes to be positioned at corresponding positions within the first image and the second image. Further, it is desirable for the corresponding shapes to be the same type of shape, for the sake of convenience in calculations. In addition, the first and second spatial parameters need only be parameters of the same type which are defined with respect to the corresponding shapes within the deformed first image Vla and the second image according to the same rule, and may be a single parameter or a plurality of parameters. Distances and angles may be employed as the first and second spatial parameters, for example.

Note that the initial positions of the corresponding shapes may be specified by any known method. For example, corresponding positions within the first image and the second image may be specified according to positions input by a user. Alternatively, the corresponding positions may be specified from characteristic positions of anatomical structures obtained by a known automatic discrimination technique.

In the image processing apparatus of the present invention, it is preferable for the evaluation function to define the degree of similarity between the deformed first image and the second image based on a total sum of the degrees of similarity among the divided images.

The image processing apparatus according to the present invention comprises: the image obtaining section that obtains a first image and a second image which are obtained by imaging the same subject at different timings; the image deformation amount estimating section that estimates an amount of deformation of the first image by deforming the first image and evaluating the degree of similarity between the deformed first image and the second image using an evaluation function that evaluates the correlative properties between the distribution of pixel values within the deformed first image and the distribution of pixel values within the second image corresponding thereto; and the image generating section that generates an image, which is the first image deformed based on the estimated amount of deformation. The evaluation function evaluates the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images. Therefore, degrees of similarity between images that include a plurality of subjects belonging to the same range of pixel values can be more accurately evaluated than had been conventionally possible, by reflecting spatial features of the subjects in the evaluation of the degrees of similarity. As a result, an image, which is the first image deformed so as to match the second image, can be generated.

BRIEF DESCRIPTION OF THE DRAWINGS

FIG. 4A is a diagram that illustrates an example of a first image (an MR image) and an example of a second image (a CT image) prior to registration.

FIG. 4B is a diagram that illustrates an example of a deformed first image (an MR image) and an example of a second image (a CT image) after registration.

FIG. 5 is a schematic block diagram that illustrates the electrical configuration of an image processing apparatus according to a second embodiment of the present invention.

BEST MODE FOR CARRYING OUT THE INVENTION

Hereinafter, embodiments of the image processing apparatus, the image processing program, and the image processing method of the present invention will be described in detail with reference to the attached drawings. The present invention may be applied to various fields in which two images, which are obtained by imaging the same subject with different modalities at different timings, undergo processes to be registered to each other. Here, a description will be given for an example in which the present invention is applied to image diagnosis in the medical field.

Figure 1:
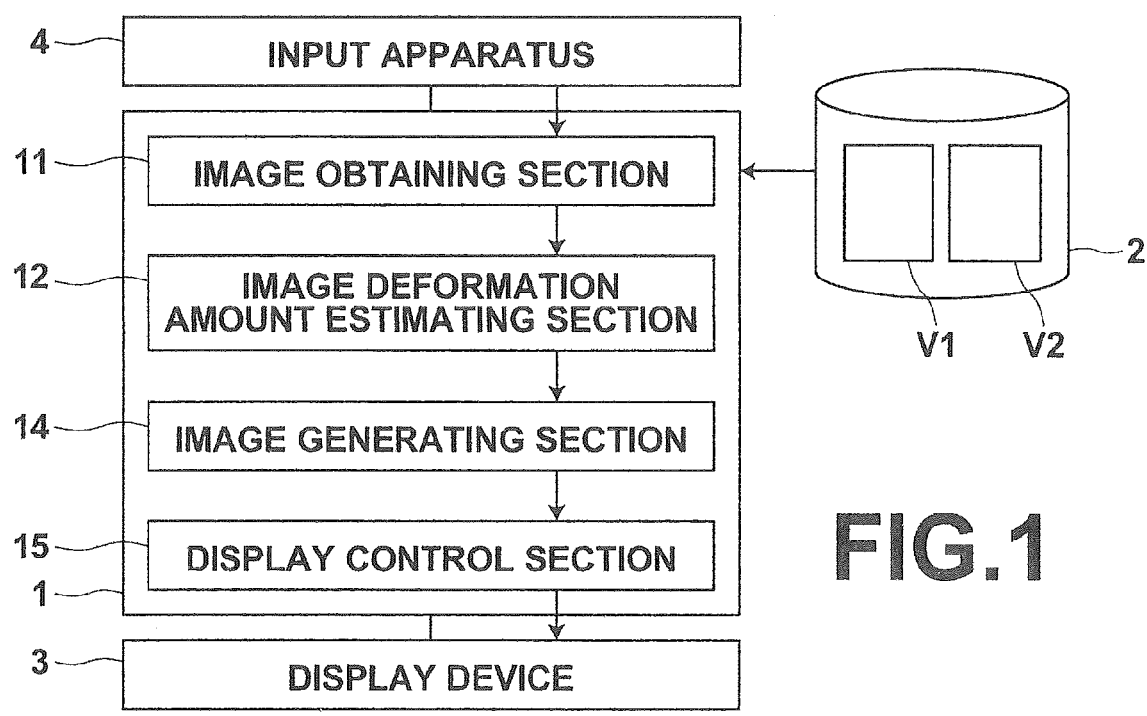
FIG. 1 is a schematic block diagram that illustrates the electrical configuration of an image processing apparatus according to a first embodiment of the present invention.

FIG. 1 illustrates the schematic configuration of an image processing apparatus, which is realized by an image processing program being installed in a work station to be utilized by a physician. The image processing apparatus 1 is equipped with a processor and a memory (neither of which are shown) as constituent elements of a standard work station, and a storage 2 such as a HDD (Hard Disk Drive). In addition, a display 3 and input devices 4 such as a mouse and a keyboard are connected to the image processing apparatus 1.

The image processing program and data referred to by the image processing program are stored in the storage 2 when the image processing program is installed, and loaded into the memory when the image processing program is started. The image processing program defines an image obtaining process, an image deformation amount estimating process, an image generating process, and a display control process, as processes to be executed by the CPU.

The general use work station functions as an image obtaining section 11, an image deformation amount estimating section 12, an image generating section 14, and a display control section 15 to be described later, by the CPU executing each of the above processes according to the definitions of the program.

A first image and a second image, which are sent from an examination division in charge of imaging, or a first image and a second image which are obtained by searching in a database, are stored in the storage 2. In the present embodiment, a first image V1 (an MR image) and a second image V2 (a CT image), which are obtained by imaging the head of a single patient at different times on the same day by different modalities during examination of the patient, are sent from an examination division. The images V1 and V2 are stored in the storage 2 after undergoing a process that uniformizes the scales of the two images V1 and V2 to that of one of the images V1 and V2, based on pixel spacing and slice spacing obtained from arbitrary data such as header data of the images V1 and V2 by a known technique. Here, FIG. 4A illustrates sample images of the first image V1 and the second image V2. In the first image V1 and the second image V2, anatomical structures such as the skull are slightly larger in the first image than the corresponding anatomical structures pictured in the second image. In addition, characteristic positions of anatomical structures, such as the borderline portion between the left and right cerebral hemispheres, are slightly shifted between the two images.

The image obtaining section 11 obtains the first image V1 and the second image V2 from the storage 2 and inputs them into the memory. In the present embodiment, if the image processing apparatus 1 detects that a predetermined registration function has been selected in a selection menu, a user is prompted to select or input data necessary to specify a first image and a second image. When the first image and the second image are specified, the image obtaining section 11 obtains the first image V1 and the second image V2 from the storage 2 and inputs them into the memory.

The image deformation amount estimating section 12 estimates an amount of deformation of the first image that will cause the subjects within the first image and the second image to match, by deforming the first image V1, and evaluating the degree of similarity between a deformed first image V1$a$ and the second image V2 using an evaluation function $S(\mu)$ that evaluates the correlative properties between the distribution of pixel values within the deformed first image V1a and the distribution of pixel values within the second image V2 corresponding thereto.

In greater detail, the image deformation amount estimating section 12 sets a set X of control points x1, x2, ..., xn that section image spaces at predetermined intervals, within each of the deformed first image V1a and the second image V2. Hereinafter, the set of control points x1, x2, ..., xn will be referred to as the control points X. Note that the image deformation amount estimating section 12 deforms the first image V1 by displacing the control points X within the first image V1 for an image deformation μ with a converting function g. Hereinafter, the control points which are the control points X that have been displaced for the amount of image deformation μ with the converting function g will be referred to as g (X, μ). An image which the first image V1 has been deformed into by displacing the control points X for the amount of image deformation p with the converting function g will be referred to as the deformed first image V1a. Note that the image deformation amount estimating section 12 sets the control points X and the amount of image deformation p by the method disclosed in D. Mattes, et al., and employs the converting function g disclosed in D. Mattes, et al. as the converting function g.

Next, the image deformation amount estimating section 12 obtains pixel values M(g(X, μ)) at control points g(X, μ) within the deformed first image V1a, and obtains pixel values F(X) at the control points X within the second image V2. Then, the image deformation amount estimating section determines the amounts of deformation μ for the control points X at which the values obtained by the evaluation function S(μ) (registration function) that evaluates the degrees of similarity among the pixel values M(g(X, μ)) at each control point g(X, μ) within the deformed first image V1a and the pixel values F(X) at each control point X within the second image V2 become maximal. The image deformation amount estimating section 12 estimates a converting function with respect to the first image V1 based on the amounts of deformation μ of the control points X at this time.

In the present embodiment, the image deformation amount estimating section 12 evaluates the degree of similarity between the deformed first image V1a and the second image V2 using an evaluation function S represented by Formula (3) to be shown below. According to the evaluation function S employed by the present embodiment, the value of the evaluation function S increases as the distributions of pixel values of the deformed first image V1a and the second image V2 are more similar. Therefore, the image deformation amount estimating section 12 judges that the amount of image deformation at which the degree of similarity between the two images is maximal (the amount of image deformation that cause the two images to become most similar) to be those, at which the amount of image deformation μ in the case that the amount of change in the value of the evaluation function S(μ) (or the absolute value of a partial derivative ∇S(9μ) with respect to the value of μ) is less than or equal to a predetermined threshold value, while varying the amount of image deformation p. Then, the image deformation amount estimating section 12 determines a converting function for deforming the first image V1 based on the amount of image deformation p. Note that the predetermined threshold may be an arbitrary value that may be considered to represent a sufficiently small value for the amount of change in the value of the evaluation function S(μ) represented by Formula (3). Various known methods may be applied as the method by which a converting function for deforming the first image V1 based on the amount of image deformation μ. Here, the method disclosed in D. Mattes, et al. is employed.

Note that here, the evaluation function is defined as that in which the degree of similarity (evaluation value) becomes greater as the degree of similarity becomes greater. Alternatively, the evaluation function may be defined as that in which the degree of similarity becomes greater as the evaluation value is smaller. In addition, the amount of image deformation μ that results in the maximum degree of similarity may be specified by any method that calculates the maximum value (or the minimum value) of an evaluation function in the non rigid registration technique, as long as the method is capable of specifying an amount of image deformation that results in the maximum (or minimum) evaluation value (degree of similarity) of the evaluation function. In addition, a plurality of evaluation values may be calculated by the evaluation function S(μ) with respect to a plurality of different amounts of image deformation μ, and the amount of image deformation μ corresponding to a specified maximum evaluation value (or a minimum evaluation value) may be specified.

The image deformation amount estimating section 12 of the present embodiment divides the deformed first image into a plurality of divided first images according to predetermined dividing conditions, divides the second image into a plurality of divided second images corresponding thereto. Then, the image deformation amount estimating section 12 evaluates the degree of similarity between the deformed first image and the second image, based on degrees of similarities which are defined to represent the similarities in the distributions of pixel values between pairs of divided images for each pair of the divided first images and the divided second image corresponding thereto.

Here, a conventional evaluation function will be described, and then the evaluation function of the present embodiment will be described in detail.

As disclosed in D. Mattes, et al., in the non rigid registration technique that registers a first image and a second image which are obtained by imaging the same subject with different modalities, the degree of similarity between distributions of pixel values of the first image and corresponding pixel values of the second image is evaluated using an evaluation function based on mutual information.

Mutual information represents the measure of correlation between two random variables f and m, based on a joint probability distribution function p(f, m) of the two random variables f and m and marginal probability distribution functions p(f) and p(m) of the two random variables f and m. Mutual information is defined by Formula (1) below as a representative example. In Formula (1), f is a discrete random variable that belongs to a set F and m is a discrete random variable that belongs to a set M. In addition, the amount of mutual information increases as the correlation between the two random variables f and m become greater. In other words, the amount of information increases to a degree that one of the variables can be estimated with a high probability if the other variable is given. Note that the amount of mutual information becomes 0 if two random variables are completely independent.

[Formula 1]

$$I(f, m) = \sum_{f \in F} \sum_{m \in M} p(f, m) \log \frac{p(f, m)}{p(m)p(f)} \quad (1)$$

The physical principles of imaging each image differ between images which are obtained by imaging the same subject with different modalities. Therefore, there are cases in which each image has different pixel values (signal values), even if the subject is of the same type. Therefore, a simple comparison of pixel values would not enable judgments regarding the similarity between two images. For example, in CT images, pixel values (CT values) become greater as the absorption rate (transmissivity) with respect to radiation. Pixel values in CT images increase in order from air, water, muscle, organs such as the liver and the heart, and bone. Meanwhile, in MR images, pixel values are determined according to nuclear magnetic resonance of hydrogen atoms included in an imaging target, and the intensity of signal values of substances are different according to imaging methods such as the T1 enhanced method and the T2 enhanced method. For example, in a T1 enhanced MR image, the pixel values become smaller in order from fat, muscle, and water. However, the order of the sizes of pixel values of fat, muscle, and water in CT images differs from that in T1 enhanced MR images. Therefore, simply comparing the pixel values of these images does not enable judgments regarding the similarity thereof.

However, even in such cases, pixel values are distributed according to common features based on the same anatomical structures at portions of the images that represent the same anatomical structures. Therefore, the distributions of pixel values of such images are correlated. D. Mattes, et al. utilize this fact to judge that two images obtained by imaging the same subject with different modalities are similar as the correlation of the distributions of pixel values of the images become greater, based on the amount of mutual information in which the pixel values of the images are random variables. In greater detail, mutual information, in which pixel values ranu of an image obtained by imaging with a first modality and which is deformed and pixel values f of an image obtained by imaging with a second modality are designated as random variables, is employed as an evaluation function, as shown in Formula (2). (Hereinafter, the pixels values of an image which is the first image deformed for an amount of image deformation μ will be expressed as m; μ, employing the amount of image deformation μ from the first image.) In Formula (2), the amount of mutual information represents the correlation between the distributions of pixel values f and m; μ of the second image and the deformed first image, respectively. Therefore, the amount of mutual information functions as a measure of the similarity between the second image and the deformed first image. Here, set F is a collection of all of the pixel values of the deformed first image, and set M is a collection of all of the pixel values of the second image.

[Formula 2]

$$S(\mu) = -\sum_{f \in F}\sum_{m \in M} p(f, m; \mu)\log\frac{p(f, m; \mu)}{p(m; \mu)p(f)} \quad (2)$$

The present inventors focused on a problem (a first problem) related to a conventional evaluation function that judges whether two images are similar based only on the correlation between distributions of pixel values of the two images, that spatial features of the images cannot be discriminated, leading to cases in which judgments regarding similarity are erroneous.

For example, the method disclosed in D. Mattes, et al. will judge that two images, in which a plurality of subjects belonging to the same range of pixel values are imaged, are similar in the case that the total number of pixels belonging to the same range of pixel values are the same within the two images, even if the numbers or the spatial positions of the plurality of subjects are different. Specifically, the pixel values of pixels that represent a pancreas and a liver within a first image obtained by imaging the thoracic region of a patient belong to the same predetermined range of pixel values. If there is a single pattern having pixel values within the predetermined range of pixel values within a second image of the thoracic region of the same patient, there is a possibility that the method disclosed in D. Mattes, et al. will judge that the two images are similar, in the case that the volume of the pattern is equal to the sum of the volumes of the liver and the pancreas within the first image.

In view of the foregoing problem, the present inventors discovered that dividing the deformed first image and the second image into corresponding regions according to predetermined dividing conditions, calculating degrees of similarity for each of the divided regions, and evaluating the degree of similarity between the first image and the second image based on the degrees of similarity of each of the divided regions is an effective measure. In this case, the possibility that a plurality of subjects which are positioned remote from each other but belong to the same range of pixel values will be included in different divided regions is high. Therefore, the probability of a plurality of subjects belonging to the same range of pixel values but are positioned remotely from each other being evaluated as correlating to each other can be suppressed. As a result, the occurrence of the aforementioned first problem can be reduced.

Note that the dividing conditions may be any method, as long as they can divide the deformed first image and the second image into regions that correspond to each other according to predetermined rules.

For example, dividing conditions that divide the deformed first image into a plurality of divided first images based on a predetermined first spatial parameter with respect to a predetermined shape, and divide the second image into a plurality of divided second images that correspond to the divided first images based on a second spatial parameter corresponding to the first spatial parameter may be considered. Note that here, the shape refers to a shape which is determined according to a predetermined rule. Examples of the shape include: a point, a line, a curve, a three dimensional shape such as a sphere, and a portion of a three dimensional shape. The shapes that correspond to each other within the first image and the second image may be arbitrarily defined as a curve, a three dimensional shape such as a sphere, or a portion of a three dimensional shape. However, it is necessary for the corresponding shapes to be positioned at corresponding positions within the first image and the second image. Further, it is desirable for the corresponding shapes to be the same type of shape, for the sake of convenience in calculations. In addition, the first and second spatial parameters need only be parameters of the same type which are defined with respect to the corresponding shapes within the deformed first image V1a and the second image according to the same rule, and may be a single parameter or a plurality of parameters. Distances and angles may be employed as the first and second spatial parameters, for example.

Note that it is necessary to uniformize the scales of the divided first images and the divided second images such that the divided first images and the divided second images represent corresponding ranges. To this end, administering a process that uniformizes the scales of the first image and the second image, based on pixel spacing and slice spacing obtained from arbitrary data such as header data, prior to setting the divided first images and the divided second images, may be considered. Note that the process that uniformizes the scales may alternatively be administered to each of the divided first images and the divided second images following the setting of the divided first images and the divided second images.

Note that the initial positions of the corresponding shapes may be specified by any known method. For example, corresponding positions within the first image and the second image may be specified according to positions input by a user. Alternatively, the corresponding positions may be specified from characteristic positions of anatomical structures obtained by a known automatic discrimination technique.

The dividing conditions in the first embodiment define that the deformed first image is divided into a plurality of divided first images according to distances from a predetermined position and that the second image is divided into a plurality of divided second images according to distances from a position corresponding to the predetermined position within the first image. The evaluation function $S(\mu)$ of the first embodiment defines a degree of divided image similarity that represents the similarity between the distributions of pixel values within a pair of divided images, for each pair of a divided first image and a divided second image corresponding thereto. The evaluation function $S(\mu)$ evaluates the degree of similarity between the deformed first image V1$a$ and the second image V2, based on the degrees of divided image similarity.

Here, various methods may be employed to calculate the degree of similarity between the deformed first image V1$a$ and the second image V2, as long as the evaluation function $S(\mu)$ calculates the degree of similarity based on the plurality of degrees of divided image similarity. As an example, the evaluation function $S(\mu)$ may be defined by the sum of the plurality of degrees of divided image similarity.

Figure 3A:
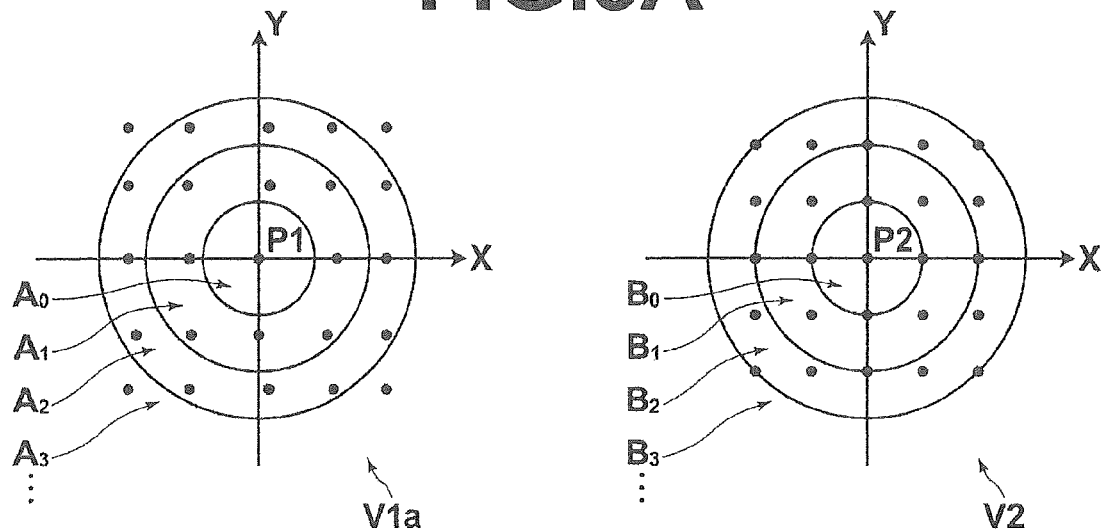
FIG. 3A is a collection of diagrams that illustrate a deformed first image and a second image which are divided by the first embodiment of the present invention, based on distances from reference points.

FIG. 3A is a collection diagrams for explaining the method by which the first and second images are divided in the first embodiment. The deformed first image V1$a$ and the second image V2 illustrated in FIG. 3A represent xy planes having the centers of three dimensional images as the origins thereof. For the purpose of the explanation, each of the control points X within the deformed first image V1$a$ are displaced only within the xy plane. As illustrated in FIG. 3A, the dividing conditions in the present embodiment are defined such that reference points P1 and P2 are respectively set in the deformed first image V1$a$ and the second image V2, and divide the deformed first image V1$a$ and the second image V2 according to ranges of distances from the reference points P1 and P2. In greater detail, the deformed first image V1$a$ and the second image V2 are divided into k spherical or hollow spherical regions that satisfy $0 \leq d < d_0$, $d_0 \leq d_1$, $d_1 \leq d_2$, ..., $d_{k-1} \leq d_k$. Then, the evaluation function $S(\mu)$ is defined by the sum of the degrees of divided image similarity between each pair of divided first images and divided second images ($A_0$, $B_0$), ($A_1$, $B_1$), ..., ($A_k$, $B_k$).

Formula (3) below is employed as the evaluation function.

[Formula 3]

$$S(\mu) = -\sum_{d \in D}\sum_{f \in F}\sum_{m \in M} p(d, f, m; \mu) \log \frac{p(d, f, m; \mu)}{p(d, m; \mu) p(d, f)} \quad (3)$$

In Formula (3), d is the range of each distance, and a set D is a collection of ranges of distances $d_0$, $d_1$, $d_2$, ..., $d_k$ (k is a positive integer). Note that depending on the case, the range of distance $0 \leq d < d_0$ will be referred to as a range of distance $d_0$. in addition, the positions of the reference points are input by a user via a manual operation of the input devices 4.

The image generating section 14 generates an image V1A, which is the first image V1 converted by a converting function determined by the image deformation amount estimating section 12.

The display control section 15 displays the image V1A generated by the image generating section 14 and the second image V2 on the display 3 such that they are capable of being compared against each other. In addition, the obtained first image V1 and the second image V2 and/or each of the images which are generated during the execution steps of the image processing program of the present invention are displayed on the display 3 according to input by the user, as necessary.

Figure 2:
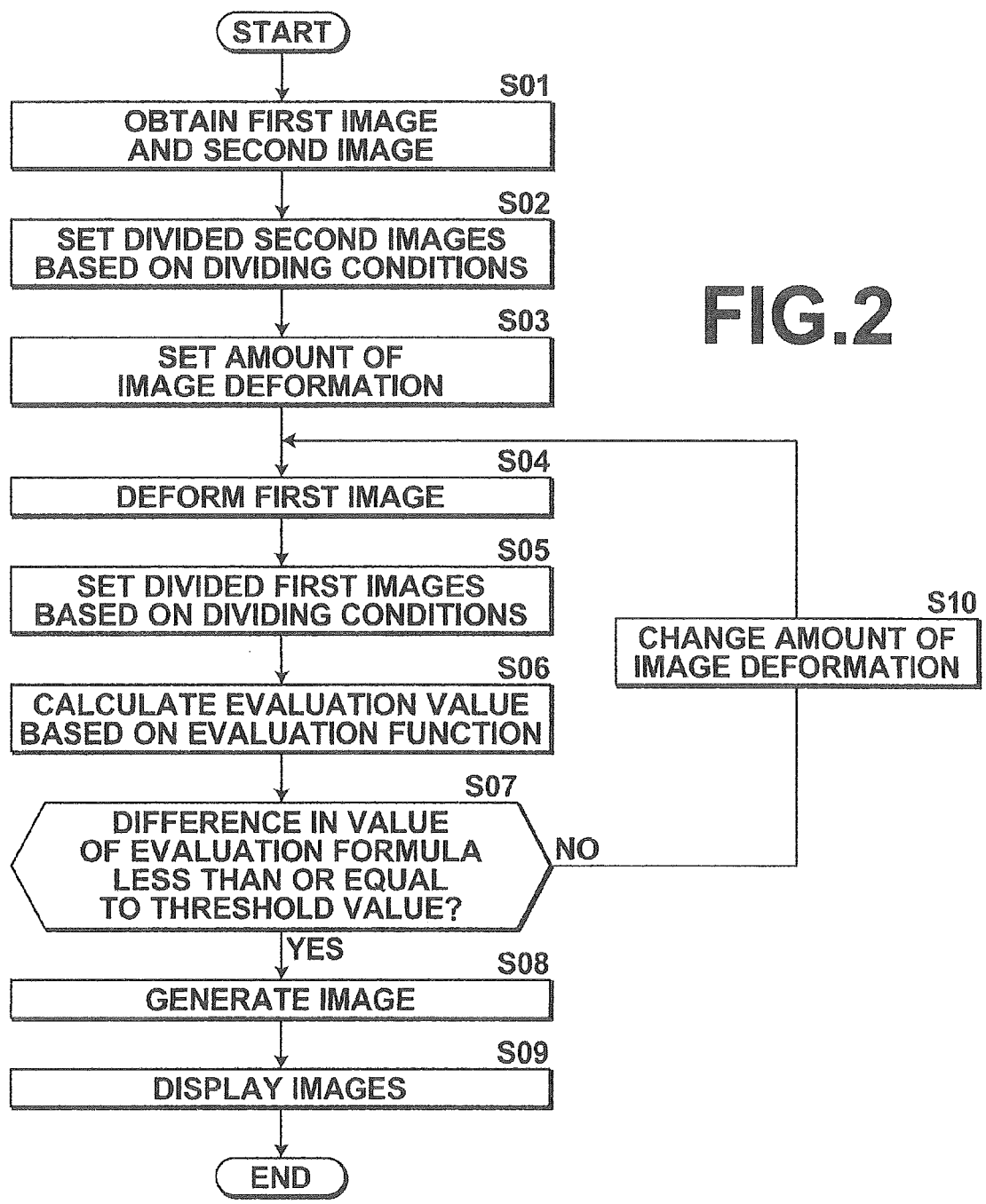
FIG. 2 is a flow chart that illustrates the steps of the operation of the image processing apparatus according to the first embodiment of the present invention.

FIG. 2 is a flow chart that illustrates the steps of the operation of the image processing apparatus according to the first embodiment of the present invention. The flow of processes process will be described with reference to FIG. 2. First, the image obtaining section 11 obtains a first image (first image data) V1 and a second image (second image data) V2, which are obtained by imaging a subject (step S01).

Next, the image deformation amount estimating section 12 sets divided second images, by dividing the second image according to dividing conditions which are set in advance. Specifically, a reference point P2 is specified in the second image V2 based on input by a user via the input devices, and the distances between the reference point P2 and each control point X are calculated. Then, the second image V2 is set as a plurality of divided second images for each predetermined range of distances $d_0$, $d_1$, $d_2$, ..., $d_k$, corresponding to distances from the reference point P2. Data that specifies each divided image are stored in the memory (step S02).

Next, the image deformation amount estimating section 12 sets an amount of image deformation $\mu$ (step S03), and employs a converting function g to deform the first image V1 (step S04).

In addition, the image deformation amount estimating section 12 sets divided first images, by dividing the first image according to dividing conditions which are set in advance. Specifically, a reference point P1 is specified in the first image V1 based on input by a user via the input devices, and the distances between the reference point P1 and each control point X are calculated (step S05). Then, the first image V1 is set as a plurality of divided first images for each predetermined range of distances $d_0$, $d_1$, $d_2$, ..., $d_k$, corresponding to distances from the reference point P1. Data that specifies each divided image are stored in the memory.

Next, the image deformation amount estimating section 12 calculates an amount of difference $|S(\mu)-S(\mu-\Delta\mu)|$ of the value of the evaluation function $S(\mu)$ expressed by Formula (3) (step S06). Thereafter, in the case that the calculated amount of difference $|S(\mu)-S(\mu-\Delta\mu)|$ is greater than a predetermined threshold value (N in step S07), a new amount of image deformation $\mu$, which is the previous amount of image deformation $\mu$ increased by a predetermined amount $\Delta\mu$, is set (step S10), and the processes of steps S03 through S06 are repeated. Note that the image deformation amount estimating section 12 may employ the absolute value of a partial derivative $|\nabla S(\mu)|$ of the evaluation function $S(\mu)$ represented by Formula (7) instead of the amount of difference $|S(\mu)-S(\mu-\Delta\mu)|$ of the evaluation function $S(\mu)$ as the evaluation value.

Meanwhile, in the case that the amount of difference $|S(\mu)-S(\mu-\Delta\mu)|$ of the evaluation function $S(\mu)$ is less than or equal to the predetermined threshold value (Y in step S07), the image deformation amount estimating section 12 obtains the amount of image deformation $\mu$ for this case as the amount of image deformation $\mu$ at which the value of the evaluation function $S(\mu)$ becomes maximal, and determines a converting function for deforming the first image based on this amount of image deformation $\mu$. The image generating section 14 employs the determined converting function to convert and reconstruct the first image, thereby generating an image V1A (step S08). Then, the display control section 15 displays the generated image V1A and the second image V2 in a manner that enables the two to be compared (step S09).

According to the first embodiment, the deformed first image V1a and the second image V2 are divided into a plurality of divided images that correspond to each other. The evaluation function $S(\mu)$ evaluates a degree of similarity based on a plurality of degrees of divided image similarity that define the correlation between the distributions of pixel values for each pair of the divided first images and the divided second images. Thereby, the probability of a plurality of subjects belonging to the same range of pixel values but are positioned remotely from each other being evaluated as correlating to each other can be suppressed, and the occurrence of the aforementioned first problem can be decreased. As a result, the degree of similarity can be evaluated more accurately, and it becomes possible to generate an image in which the first image matches the second image more favorably.

In addition, the dividing conditions divide the deformed first image and the second image according to a single spatial parameter, which are the distances from the reference points. Therefore, the calculation load for calculating the degree of similarity is not increased unnecessarily, by storing a plurality of corresponding divided first images and second images for each predetermined range of distances $d_0, d_1, d_2, \ldots, d_k$, according to distances from the reference point P2. In addition, because the first spatial parameters are distances from a point that functions as a reference, setting of the shapes that function as a reference within the first image and the second image is facilitated.

As a further modification to the dividing conditions of the first embodiment, the deformed first image V1a and the second image V2 may be divided according to angles instead of distances. A case in which the deformed first image V1a and the second image V2 are divided by predetermined angular ranges according to angles $\theta$ with respect to shapes that function as references in this manner may be considered. Note that in this case, Formula (3), in which the distances d are replaced by angles $\theta$, may be employed as the evaluation function.

In addition, the probability that the number of subjects included in each divided image will become smaller is higher as the units of division of the divided first images and the divided second images become smaller. Therefore, the occurrence of the first problem can be further reduced, and the degree of similarity between the deformed first image and the second image can be evaluated more precisely.

Figure 3B:
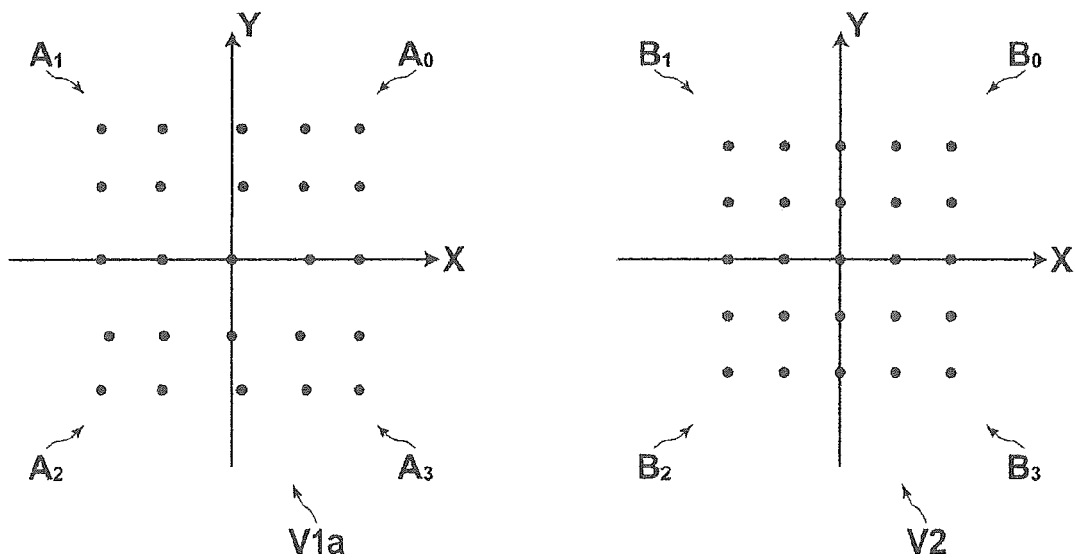
FIG. 3B is a collection of diagrams that illustrate a deformed first image and a second image which are divided by the first embodiment of the present invention, based on angles from the x axis.

FIG. 3B illustrates an example in which a deformed first image V1a and a second image V2 are divided based on angles $\theta$ from the x axis (a predetermined axis) within an xy plane (a predetermined plane) as another example of a method for dividing the first and second images in the first embodiment. The deformed first image V1a and the second image V2 of FIG. 3B represent xy planes that pass through the origins of three dimensional images. For the purpose of the explanation, each of the control points X within the deformed first image Via are displaced only within the xy plane. Note that the angles $\theta$ can be obtained as angles $\theta$ in the case that the two images V1a and V2 are respectively represented by a cylindrical coordinate system.

In FIG. 3B, the deformed first image V1a is divided into divided first images $A_0, A_1, A_2$, and $A_3$, and the second image V2 is divided into divided second images $B_0, B_1, B_2$, and $B_3$, in four ranges, which are $0 \leq \theta < 90°$, $90 \leq \theta < 180°$, $180 \leq \theta < 270°$, and $270 \leq \theta < 360°$. Alternatively, the ranges of $\theta$ may be set as desired, to divide the deformed first image V1a and the second image V2 into k images corresponding to angles $\theta$ with respect to a shape that functions as a reference, in ranges of $0 \leq \theta < \theta_0$, $\theta_0 \leq \theta < \theta_1$, $\theta_1 \leq \theta < \theta_2$, \ldots, $\theta_{k-1} \leq \theta < \theta_k$.

As described above, the dividing conditions may be those that divide the deformed first image and the second image according to angles from a reference shape, which is a single spatial parameter. In this case, data that specify each divided first image and each divided second image for each predetermined angular range $\theta_0, \theta_1, \theta_2, \ldots, \theta_k$ are stored in the memory. Thereby, the calculation load for calculating the degree of similarity between the deformed first image and the second image is not increased unnecessarily.

Alternatively, the deformed first image V1a and the second image V2 may be divided based on arbitrary angles ($0 \leq \theta < \theta_0$, $\theta_0 \leq \theta < \theta_1$, $\theta_1 \leq \theta < \theta_2$, \ldots $\theta_{k-1} \leq \theta < \theta_k$) with respect to the x axis, and the divided images may be further divided based on arbitrary angles ($0 \leq \beta < \beta_0$, $\beta_0 \leq \beta < \beta_1$, $\beta_1 \leq \beta < \beta_2$, \ldots, $\beta_{m-1} \leq \beta < \beta_m$) with respect to the z axis (m is an integer 0 or greater). In the case that the deformed first image V1a and the second image V2 are divided based on angles with respect to each of two axes in this manner, the deformed first image V1a and the second image can be divided into regions that are adjacent to each other in three dimensional spaces. Therefore, the first problem can be more favorably suppressed, and the degree of similarity between the deformed first image and the second image can be evaluated more precisely.

In addition, the divided first images may be set by dividing the deformed first image V1a based on distances, then further dividing the deformed first image V1a based on angles.

In addition, in the present embodiment, the amount of mutual information expressed by Formula (2) is employed as an item that represents the measure of correlation between two images obtained by imaging the same subject with different modalities. However, the item that represents the measure of correlation between the two images may be various known variations of the above, as long as it includes the amount of mutual information. In addition, the evaluation function may have other items such as that which defines limiting conditions for the smoothness of deformation, and may be various known variations of the above.

Next, a second embodiment of the present invention will be described. FIG. 5 is a schematic functional block diagram of the second embodiment. As illustrated in FIG. 5, an image deformation amount estimating section 12 is equipped with a probability data obtaining section 13 that obtains the certainty of combinations of corresponding pixel values of a first image and a second image as probability data, in the second embodiment. The second embodiment differs from the first embodiment in that the item in an evaluation function that represents the measure of the degree of similarity is weighted by the probability data.

The processes performed by the second embodiment other than the evaluation of the degree of similarity between a deformed first image and the second image employing the evaluation function $S(\mu)$ are the same as those of the first embodiment. In addition, the functions of each of the functional blocks are also the same. Hereinafter, a description will be given mainly regarding points that differ from the first embodiment, and descriptions of points which are the same as the first embodiment will be omitted.

The present inventors focused on the fact that a conventional evaluation function such as that expressed by Formula (2) does not evaluate the certainty of combinations of pixel values obtained by the types of modalities at all. This leads to a problem (a second problem) that such certainty is not reflected when evaluating calculated degrees of similarity, even in cases in which it is predicted that pixel values of the second image corresponding to pixel values of the deformed first image will be within a range which is determined to a certain degree.

In view of the foregoing second problem, the present inventors discovered that incorporating probability data that represents the certainty of combinations of pixel values of the deformed first image and the second image into an evaluation function is an effective measure. Probability data $P_L(m; \mu|f)$ was applied as the item that represents the measure of similarity between the deformed first image and the second image in Formula (3), as shown in Formula (4). That is, the item that represents the measure of similarity between the deformed first image and the second image is weighted by the probability data $P_L(m; \mu|f)$ that represents the certainty of the combination of the two images for each combination of pixel values of the deformed first image and the second image, according to the certainty of the combination of the pixel values of the two images.

As shown in Formula (4), in the evaluation function employed by the present embodiment, the item that represents the measure of similarity between the deformed first image and the second image is weighted by the probability data $P_L(m; \mu|f)$ that represents the certainty of the combination of the two images for each combination of pixel values of the deformed first image and the second image, according to the certainty of the combination of the pixel values of the two images. Note that as illustrated in FIG. 3A, the dividing conditions in the second embodiment are defined such that reference points P1 and P2 are respectively set in the deformed first image V1a and the second image V2, and divide the deformed first image V1a and the second image V2 according to ranges of distances from the reference points P1 and P2. In addition, in the evaluation function $S(\mu)$ represented by Formula (4), degrees of similarity (degrees of divided image similarity) of pairs $(A_0, B_0), (A_1, B_1), \ldots, (A_k, B_k)$ of the divided first images and the divided second images are defined as items in which mutual information of each pair of images is weighted by the probability data described above.

[Formula 4]

$$S(\mu) = -\sum_{d \in D} \sum_{f \in F} \sum_{m \in M} p_L(m; \mu | f) p(d, f, m; \mu) \log \frac{p(d, f, m; \mu)}{p(d, m; \mu) p(d, f)} \quad (4)$$

The probability data $P_L(m; \mu|f)$ may be any type of data as long as it defines the certainty of the combinations of corresponding pixel values within an image obtained by imaging a predetermined subject with a first modality and an image obtained by imaging the same type of predetermined subject with a second modality. Here, the predetermined subject may be the same as or different from the subjects pictured in the first image V1 and the second image V2.

The present embodiment defines the certainty of combinations of corresponding pixel values of an image obtained by imaging with a first modality and an image obtained by imaging with a second modality as a conditional probability, in which pixel values of the second image become m; based on phenomena that pixel values of corresponding pixels in the first image become f. Note that as shown in Formula (5) below, the conditional probability can be calculated from a joint probability distribution function $P_L(f, m; \mu)$ and a marginal probability distribution function $P_L(f)$ of the random variable f.

[Formula 5]

$$p_L(m; \mu | f) = \frac{p_L(f, m; \mu)}{p_L(f)} \quad (5)$$

In the present embodiment, the probability data obtaining section 13 obtains the pixel values f (f∈F) of all of the control points within an image, which is the first image deformed for an amount of image deformation µ, and the pixel values m(m∈M) of each corresponding control point within the second image. Then, the joint probability distribution function $P_L(f, m; \mu)$ is obtained by investigating, for each pixel value f(f∈F) of the control points, the distribution of the pixel values m(m∈M) at the corresponding control points. Thereafter, the marginal probability distribution function $P_L(f)$ is obtained by investigating the distribution of the pixel values f of each control point. Finally, the probability data $P_L(m; \mu|f)$ is obtained based on Formula (5).

Note that a first reference image obtained by imaging a predetermined subject with a first modality and a second reference image obtained by imaging the same predetermined subject with a second modality may be employed to calculate the aforementioned conditional probability. Note that it is not necessary for the predetermined subject to be of the same type as the subject within the first image and the second image. However, it is preferable for the subjects which are pictured in the first reference image and the second reference image to be of the same type as the subjects pictured in the first image and the second image, in order to more accurately calculate the probability data. In addition, there may be a single pair or a plurality of pairs of the first reference image and the second reference image. It is preferable for a plurality of pairs of the first reference image and the second reference image to be employed to calculate the conditional probability, because it is considered that the certainty of the combinations of pixel values can be more accurately estimated in such a case.

In addition, the calculation or the obtainment of the probability data $P_L(m; \mu|f)$ may be performed at an arbitrary timing as long as it is prior to a process for calculating the amount of image deformation that results in the maximum value of the evaluation function $S(\mu)$.

Figure 6:
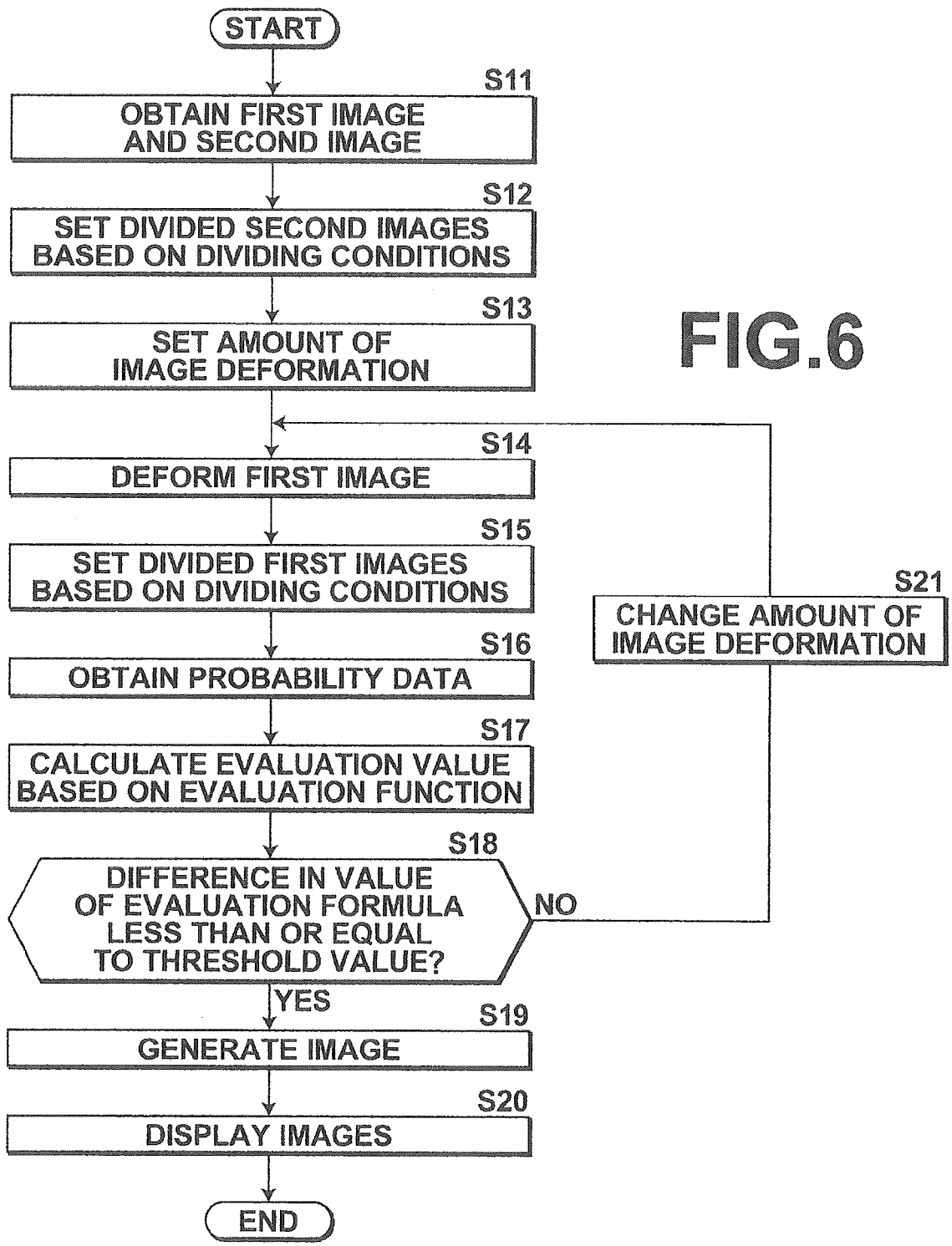
FIG. 6 is a flow chart that illustrates the steps of the operation of the image processing apparatus according to the second embodiment of the present invention.

FIG. 6 is a flow chart that illustrates the steps of the operation of the image processing apparatus according to the second embodiment. The flow of processes process will be described with reference to FIG. 6. First, the image obtaining section 11 obtains a first image (first image data) V1 and a second image (second image data) V2, which are obtained by imaging a subject (step S11).

Next, an image deformation amount estimating section 12 sets divided second images, by dividing the second image according to dividing conditions which are set in advance. Specifically, a reference point P2 is specified in the second image V2 based on input by a user via the input devices, and the distances between the reference point P2 and each control point X are calculated. Then, the second image V2 is set as a plurality of divided second images for each predetermined range of distances $d_0, d_1, d_2, \ldots, d_k$, corresponding to distances from the reference point P2. Data that specifies each divided image are stored in the memory (step S12).

Next, the image deformation amount estimating section 12 sets an amount of image deformation µ (step S13), and employs a converting function g to deform the first image V1 (step S14).

In addition, the image deformation amount estimating section 12 sets divided first images, by dividing the first image according to dividing conditions which are set in advance. Specifically, a reference point P1 is specified in the first image V1 based on input by a user via the input devices, and the distances between the reference point P1 and each control point X are calculated (step S15). Then, the first image V1 is set as a plurality of divided first images for each predetermined range of distances $d_0, d_1, d_2, \ldots, d_k$, corresponding to distances from the reference point P1. Data that specifies each divided image are stored in the memory.

Next, the image deformation amount estimating section 12 obtains each pixel value of the deformed first image V1a and the second image V2, and calculates a joint probability distribution $p(f, m; \mu)$ and marginal probability distributions $p(f), p(m; \mu)$. The probability data obtaining section 13 obtains probability data $P_L(m; \mu|f)$ by calculating a conditional probability in the manner described above, based on the calculated joint probability distribution $p(f, m; \mu)$, the marginal probability distributions $p(f), p(m; \mu)$, and the probability data $P_L(m; \mu|f)$ (step S16). Next, the image deformation amount estimating section 12 calculates an amount of difference $|S(\mu)-S(\mu-\Delta\mu)|$ of the value of the evaluation function $S(\mu)$ expressed by Formula (4) (step S17). Thereafter, in the case that the calculated amount of difference $|S(\mu)-S(\mu-\Delta\mu)|$ is greater than a predetermined threshold value (N in step S18), a new amount of image deformation $\mu p+\Delta\mu$, which is the previous amount of image deformation $\mu$ increased by a predetermined amount $\Delta\mu$, is set (step S21), and the processes of steps S13 through S18 are repeated. Note that the image deformation amount estimating section 12 may employ the absolute value of a partial derivative $|\nabla S(\mu)|$ of the evaluation function $S(\mu)$ instead of the amount of difference $|S(\mu)-S(\mu-\Delta\mu)|$ of the evaluation function $S(\mu)$ as the evaluation value.

Meanwhile, in the case that the amount of difference $|S(\mu)-S(\mu-\Delta\mu)|$ of the evaluation function $S(\mu)$ is less than or equal to the predetermined threshold value (Y in step S18), the image deformation amount estimating section 12 obtains the amount of image deformation $\mu$ for this case as the amount of image deformation $\mu$ at which the value of the evaluation function $S(\mu)$ becomes maximal, and determines a converting function for deforming the first image based on this amount of image deformation $\mu$. An image generating section 14 employs the determined converting function to convert and reconstruct the first image, thereby generating an image V1A (step S19). Then, the display control section 15 displays the generated image V1A and the second image V2 in a manner that enables the two to be compared (step S20).

According to the present embodiment, the item that represents the similarity between the deformed first image and the second image in the evaluation function is weighted by the probability data that represents certainty of combinations of pixel values of the control points in the deformed first image and the second image. Therefore, combinations of the pixel values of the control points within an image obtained by a first modality and pixel values of the control points within an image obtained by a second modality which are actually impossible can be weighted such that the degree of similarity becomes low. Thereby, degrees of similarity can be more accurately evaluated, and as a result, an image, which is the first image deformed so as to match the second image, can be generated more favorably.

In addition, the item that represents the similarity between corresponding pixel values of an image obtained by imaging with a first modality and an image obtained by imaging with a second modality is weighted by a conditional probability, in which pixel values of the image obtained by the second modality become m; $\mu$ based on phenomena that pixel values of corresponding pixels in the image obtained by the first modality become f. Therefore, the degree of similarity between the two images can be more accurately calculated according to the certainty of combinations of the pixel values of the two images.

In the case that the conditional probability is calculated based on each of the pixel values of the first image and the second image, the probability data can be set only from data regarding the distributions of pixel values of the two images. Therefore, collection and analysis of data in order to set the probability data is obviated, and application to the evaluation function is facilitated. In addition, the efficiency of calculations is high, because both the amount of mutual information and the conditional probability can be calculated based on the joint probability distribution $p(f, m; \mu)$ and the marginal probability distribution $p(f)$.

The second embodiment may be modified such that the probability data is that in which a first range of pixel values in the case that a subject of a predetermined type is imaged with a first modality and a second range of pixel values in the case that a subject of the predetermined type is imaged with a second modality are correlated for a plurality of types of subjects, and the evaluation function weights the degree of similarity between the deformed first image and the second image to be low in the case that the pixel values of the deformed first image and the second image do not satisfy both the first range of pixel values and the second range of pixel values corresponding to the first range of pixel values. Note that in the present specification, weighting the degree of similarity to be low means weighting to decrease the degree of similarity in the case that an evaluation function that evaluates the deformed first image and the second image as being more similar as the degree of similarity is greater is employed, and means weighting to increase the degree of similarity in the case that an evaluation function that evaluates the deformed first image and the second image as being more similar as the degree of similarity is smaller is employed.

The evaluation function to the above modification to the second embodiment may be defined as shown in Formula (6) below, for example. In the following example, each of the pixel values $f(f \in F)$ of an image obtained by a second modality is correlated with a range $m_{min}^f \leq m(\mu) \leq m_{max}^f$ of possible pixel values of an image obtained by a first modality and stored. In the case that the pixel values $m(\mu)$ of the second image belong within the range $m_{min}^f \leq m(\mu) m_{max}^f$ correlated with pixel values f (the first range of pixel values), the item that represents the measure of correlation between the first image and the second image in the evaluation function is weighted by 1. In other cases, it is judged that the combination of pixel values is that which is not actually possible, and the item that represents the measure of correlation between the first image and the second image in the evaluation function is weighted by 0 to decrease the degree of similarity.

[Formula 6]

$$p_L(m; \mu \mid f) = \begin{cases} 1, & m_{min}^f \leq m(\mu) \leq m_{max}^f \\ 0, & \text{otherwise} \end{cases} \quad (6)$$

In the modification to the second embodiment described above, the corresponding ranges of pixel values of the first image and the second image may be determined by known data, obtained by analyzing test images which are obtained in advance. For example, the ranges of pixel values of images of each of a plurality of types of subjects such as water, air, and anatomical structures (or elements that constitute anatomical structures) obtained by the first modality are correlated with ranges of pixel values of corresponding targets, such as water, air, and anatomical structures obtained by the second modality, and are stored as probability data. Then, the image deformation amount estimating section 12 may decrease the degree of similarity for combinations of pixel values which are not any of the combinations of the ranges of pixel values correlated in the probability data. In this case, the probability data sets corresponding ranges of pixel values based on known data regarding the pixel values of pairs of images. Therefore, the probability data can be defined more accurately.

In addition, the corresponding ranges of pixel values of pixel values within the first image and the second image may be determined from theoretical pixel values which are estimated based on the imaging principles of each modality. For example, pixel values are estimated for cases that each of a plurality of types of targets that may be subjects are imaged by each modality, correlated with each type of target, and stored. For example, ranges of pixel values of images of each of a plurality of types of subjects such as water, air, and anatomical structures (or elements that constitute anatomical structures) obtained by the first modality and the second modality are estimated based on the imaging principles of each modality. Then, the estimated ranges of pixel values of images obtained by the first modality and the estimated ranges of pixel values of images obtained by the second modality are correlated for each target and stored. Then, the degree of similarity for combinations of pixel values which are not any of the combinations of the ranges of pixel values correlated in the probability data may be decreased. In this case, the probability data sets corresponding ranges of pixel values based on data regarding the pixel values of pairs of images which are estimated from imaging principles. Therefore, the probability data can be defined more accurately.

The probability data described above may be scaled (normalized) to further adjust weighting. In this case, the item that represents the correlation between the first and second reference images can be prevented from becoming excessively great (or excessively small) in cases that the conditional probability assumes an extremely low value, for example. In addition, various known techniques may be applied to adjust the weighting.

For example, it is preferable for the probability data to be normalized in the case that the conditional probability is employed as the probability data, in order to reduce the influence of the shape of the distributions of pixel values. A probability density function that employs pixel values as random variables is an element in calculating the conditional probability. The probability density function assumes a small value in the case that a distribution of pixel values is flat, and assumes a large value in the case that a distribution of pixel values is steep and has concentrated portions. That is, the probability density function has a property that it varies according to the shapes of distributions of pixel values. For this reason, first, each of the pixel values f (f∈F) of an image obtained by a second modality is correlated with a range $m_{min}^f \leq m(\mu) \leq m_{max}^f$ of possible pixel values of an image obtained by a first modality and stored. The distribution of pixel values of the first reference image correlated with each pixel value f from among the pixel values f(f∈F) of the image obtained by the second modality is approximated to a uniform distribution, to calculate a probability density function $P_U(m)$ (=$m_{max}^f - m_{min}^f$) of the first reference image. Then, the probability data is further weighted by a reciprocal $A_m$ of the probability density function $P_U(m)$, as shown in Formula (7).

[Formula 7]

$$p_L(m; \mu | f) = \frac{p_L(f, m; \mu)}{p_L(f)p_U(m)} = A_m \frac{p_L(f, m; \mu)}{p_L(f)} \qquad (7)$$

In this case, the influence of the shapes of the distributions of pixel values $m_{min}^f < m(\mu) < m_{max}^f$ which are correlated with the pixel values f of the image obtained by the second modality can be suppressed. Thereby, the certainty of combinations of pixel values of the image obtained by the first modality and the pixel values of the image obtained by the second modality can be more favorably reflected, and weighting can be performed more appropriately.

The embodiments described above are merely examples, and the entirety of the above description should not be utilized to interpret the technical scope of the present invention in a limiting manner.

In addition, various changes to the system configurations, the hardware configurations, the process flows, the module configurations, the user interfaces, the specific contents of the processes, etc., of the above embodiments are included within the technical scope of the present invention as long as such changes do not stray from the spirit of the present invention.

The image processing apparatus 1 may be that in which a plurality of computers divide the functions of each of the means. In addition, various known apparatuses may be applied as the devices that constitute the system, such as the input devices and the display.

What is claimed is:
1. An image processing apparatus, comprising:
an image obtaining section that obtains a first image and a second image which are obtained by imaging the same subject at different timings;
an image deformation amount estimating section that estimates an amount of deformation of the first image by deforming the first image and evaluating the degree of similarity between the deformed first image and the second image using an evaluation function that evaluates the correlative properties between the distribution of pixel values within the deformed first image and the distribution of pixel values within the second image corresponding thereto; and
an image generating section that generates an image, which is the first image deformed based on the estimated amount of deformation;
the evaluation function evaluating the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images; and
the dividing conditions dividing the deformed first image into a plurality of divided first images based on a predetermined first spatial parameter, and dividing the second image into a plurality of divided second images that correspond to the divided first images based on a second spatial parameter corresponding to the first spatial parameter.
2. An image processing apparatus as defined in claim 1, wherein:

the first spatial parameter represents the distance from a predetermined shape within the first image, and the second spatial parameter represents the distance from a shape within the second image corresponding to the predetermined shape.

3. An image processing apparatus as defined in claim 2, wherein:
the predetermined shape is a point; and
the dividing conditions are those that divide the first image for each range of the first spatial parameter according to the first spatial parameter, and divide the second image for each range of the second spatial parameter, which corresponds to the range of the first spatial parameter.

4. An image processing apparatus as defined in claim 1, wherein:
the first spatial parameter represents an angle with respect to a predetermined shape within the first image, and the second spatial parameter represents an angle with respect to a shape within the second image corresponding to the predetermined shape.

5. An image processing apparatus as defined in claim 4, wherein:
the predetermined shape is a predetermined axis within the first image;
the first spatial parameter represents an angle from the predetermined axis within the first image; and
the second spatial parameter represents an angle from an axis within the second image corresponding to the predetermined axis.

6. An image processing apparatus as defined in claim 1, wherein:
the evaluation function defines the degree of similarity between the deformed first image and the second image based on a total sum of the degrees of similarity among the divided images.

7. An image processing apparatus as defined in claim 1, wherein:
the evaluation function represents an amount of mutual information, in which the pixel values of the deformed first image and the pixel values of the second image are discrete random variables.

8. An image processing method to be executed by an image processing apparatus comprising an image obtaining section, an image deformation amount estimating section, and an image generating section, comprising:
obtaining a first image and a second image which are obtained by imaging the same subject at different timings;
estimating an amount of deformation of the first image by deforming the first image and evaluating the degree of similarity between the deformed first image and the second image using an evaluation function that evaluates the correlative properties between the distribution of pixel values within the deformed first image and the distribution of pixel values within the second image corresponding thereto; and
generating an image, which is the first image deformed based on the estimated amount of deformation;
the evaluation function evaluating the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images; and
the dividing conditions dividing the deformed first image into a plurality of divided first images based on a predetermined first spatial parameter, and dividing the second image into a plurality of divided second images that correspond to the divided first images based on a second spatial parameter corresponding to the first spatial parameter.

9. A non transitory computer readable medium having an image processing program stored therein, the program causing a computer to function as:
an image obtaining section that obtains a first image and a second image which are obtained by imaging the same subject at different timings;
an image deformation amount estimating section that estimates an amount of deformation of the first image by deforming the first image and evaluating the degree of similarity between the deformed first image and the second image using an evaluation function that evaluates the correlative properties between the distribution of pixel values within the deformed first image and the distribution of pixel values within the second image corresponding thereto; and
an image generating section that generates an image, which is the first image deformed based on the estimated amount of deformation;
the evaluation function evaluating the degree of similarity between the deformed first image and the second image, based on degrees of similarities of divided images that represent degrees of similarities among the distributions of pixel values of each pair of divided first images and divided second images, which respectively are a plurality of images that the deformed first image is divided into according to predetermined dividing conditions and a plurality of images that the second image is divided into such that they correspond to the divided first images; and
the dividing conditions dividing the deformed first image into a plurality of divided first images based on a predetermined first spatial parameter, and dividing the second image into a plurality of divided second images that correspond to the divided first images based on a second spatial parameter corresponding to the first spatial parameter.

* * * * *